(12) United States Patent
Amar

(10) Patent No.: US 6,520,183 B2
(45) Date of Patent: Feb. 18, 2003

(54) DOUBLE ENDOBRONCHIAL CATHETER FOR ONE LUNG ISOLATION ANESTHESIA AND SURGERY

(75) Inventor: David Amar, Hillcrest, NY (US)

(73) Assignee: Memorial Sloan-Kettering Cancer Center, New York, NY (US)

( * ) Notice: Subject to any disclaimer, the term of this patent is extended or adjusted under 35 U.S.C. 154(b) by 0 days.

(21) Appl. No.: 09/878,788

(22) Filed: Jun. 11, 2001

(65) Prior Publication Data

US 2002/0185135 A1 Dec. 12, 2002

(51) Int. Cl.[7] ............................................ A61M 16/00
(52) U.S. Cl. ................ 128/207.14; 128/911; 604/96.01
(58) Field of Search ........................ 128/207.14, 207.15, 128/207.16, 207.17, 911; 604/96.01, 101.01, 101.04

(56) References Cited

U.S. PATENT DOCUMENTS

| | | | | |
|---|---|---|---|---|
| 5,309,906 A | * | 5/1994 | LaBombard | 128/207.14 |
| 5,964,796 A | * | 10/1999 | Imran | 607/122 |
| 6,115,523 A | * | 9/2000 | Choi et al. | 385/116 |
| 6,159,158 A | * | 12/2000 | Lowe | 600/529 |
| 6,443,156 B1 | * | 9/2002 | Niklason et al. | 128/207.14 |

* cited by examiner

*Primary Examiner*—Ronald Capossela
(74) *Attorney, Agent, or Firm*—Klauber & Jackson

(57) ABSTRACT

A double endobronchial catheter that is suited for one lung isolation anesthesia and surgery that has an outer sheath that is adapted to be introduced into the patient such that the distal end of the sheath is positioned within the patient and the proximal end remains exterior of the patient. A pair of catheters are slidingly retained in separate lumens within the outer sheath lumen. Each of the catheters has an inflatable balloon at the distal end thereof with the proximal ends extending outwardly from the proximal end of the outer sheath. A stylet is removably positioned within each of the catheters so that each catheter can be manipulated independently of the other catheter within the confines of the outer sheath so that the distal ends of the catheters can be positioned at a site within the bronchi of the patient and, upon inflation of the balloons, one of the patient's lungs can be isolated and ventilation and anesthesia administered to the other lung.

17 Claims, 3 Drawing Sheets

DOUBLE ENDOBRONCHIAL CATHETER FOR ONE LUNG ISOLATION ANESTHESIA AND SURGERY

BACKGROUND OF THE INVENTION

The present invention relates to catheters, and more particularly, to a double endobronchial catheter that is used to isolate one lung of a patient during anesthesia and surgery.

There are many operations that are carried out or performed today on a patient that require one lung of that patient to be isolated, that is, one of the patient's lungs must be kept relatively immobilized during the operation so that the surgery can be performed. Typical of such operations include thoracoscopic lung surgery, minor or major lung resection, thoracic aorta repair or reconstruction, esophageal surgery and anterior thoracic spine surgery.

The need to isolate such lungs in order to operate stem from the very nature of a surgical operation performed under general anesthesia. In such operations, an anesthesia apparatus actually breathes for the patient by means of an anesthesia ventilator that acts in conjunction with an anesthesia machine. The anesthesia ventilator provides a timed, intermittent flow of gas to the patient to force that gas into the patient to expand the lungs, while the gas is expelled from the lungs as the lungs deflate. The anesthesia machine adds the anesthetic, in the form of a vapor, to the gas so that the anesthetic laden gas is provided to the patient to carry out the induction and maintenance of anesthesia in the patient during the operation. Thus under normal operation, both lungs are continually expanded and contracted during the inhalation and exhalation of the anesthetic laden gases in accordance with the normal cycling of the anesthesia ventilator.

Obviously, with the aforelisted operations where it is undesirable to have one of the lungs in motion, it becomes necessary to isolate that lung for the entire operation so that it is not subject to the normal expansion and contraction that is caused by the anesthesia ventilator. Therefore, the lung to be operated on is normally isolated by occluding the bronchus of that lung such that the anesthesia machine breathes the anesthetic laden gas into and from the other lung without affecting the lung subject to the operation. Thus the patient can be anesthetized and the operation can be carried out on the isolated lung. One of the difficulties, however, is to fully and effectively occlude the mainstream bronchus leading into the lung that is to be subject to the surgery.

One of the more common techniques currently used to provide the necessary isolation for one lung is through the use of a double lumen endotracheal tube. With the use of a double lumen endotracheal tube, however, there are certain drawbacks to its use.

In particular, there can be a considerable drawback in its insertion in the event of an unanticipated difficult airway visualization or the presence of a paralyzed vocal cord. Further, the anesthesiologist may choose to abandon the use of a double endotracheal tube in the event some anatomical problem is encountered in its placement, such as tracheal narrowing, which could preclude the proper positioning of the double lumen endotracheal tube. In addition, with many procedures, there is a difficult situation where the risk of gastric aspiration is high and a double lumen endotracheal tube needs to be replaced by a standard single lumen tube after the conclusion of the operation.

SUMMARY OF THE INVENTION

Thus, in accordance with the present invention, there is provided a double endobronchial catheter that is relatively easy to use with a patient and yet which provides effective isolation of a single lung of the patient so that surgery can be performed on that lung without interference caused by movement of that lung during the normal general anesthesia involving the ventilation of the lung.

With the present invention, there is an outer sheath that can be intubated into the trachea of the patient either external to a standard single lumen endotracheal tube or embodied within it and which outer sheath has a plurality of individual lumens formed therein. In the preferred embodiment, there are but two lumens within the outer sheath and they are formed by being molded into the outer sheath with an integrally molded divider separating the individual lumens. Within each of those two lumens there is positioned a catheter that is free to slide within the individual lumens of the outer sheath. In order to allow ease of movement within the lumens of the outer sheath, the outer surfaces of each catheter is preferably coated with a lubricious material, such as silicone. At the distal end of both of the catheters, there is an inflatable balloon and an inflation passage is provided so that each balloon can be individually inflated by the user by means of an inflation device at or near the proximal end of each catheter.

The individual catheters are flexible and can be manipulated by the user proximal to the patient after intubation of the outer sheath and a stylet can be associated with each catheter that passes through each of the catheters to aid in the manipulation of the individual catheters. In the preferred embodiment, the stylets are removable from the catheter after the proper positioning of the catheters.

Each of the catheters also includes a suction passageway that comprises a means of applying suction at the distal end of the catheters by a vacuum source or system connected to the proximal end of the catheters so that suction can be applied to a lung as desired.

In accordance with the present invention, there is provided a double endobronchial catheter that can be used in many instances where the prior art double lumen endotracheal tube is not appropriate or feasible. For example, the present invention can be a smaller device than the current double lumen endotracheal tube and thus can be used where a double endotracheal tube cannot be intubated through the vocal cords because of unanticipated difficult airway visualization or the presence of a paralyzed vocal cord. Too, the present invention can be used if the physician encounters lower airway anatomical problems, such as narrowing of the passageways, that would otherwise preclude the use of a double lumen endotracheal tube. Further, in the event of a patient who cannot open the mouth well or one with a known difficult intubation so as to make the placement of a double lumen endotracheal tube difficult, the present invention can be used in an "awake fiberoptic intubation" using a single lumen endotracheal tube followed by the use of the present double endobronchial catheter.

Also, due to the presence of through orifices in the catheters used with the present invention, in cases where selective lobar blockade is desired (partial one-lung collapse), the present double endobronchial catheter can be used and later the lung converted to full collapse if so desired. Partial collapse may be chosen in patients with marginal pulmonary function reserve prior to surgery that will not tolerate full collapse.

In addition, the present double endobronchial catheter can be made with smaller, softer, lower pressure balloons than those found on the present single or double lumen endotracheal tubes and thus can be used where intubation of the former tubes is difficult due to the anatomy of the patient. Too, with the use of the present invention, there is no need to replace a double lumen endotracheal tube with a single lumen endotracheal tube and thus the risk of aspiration is virtually eliminated where caused by that action.

Other features of the overall endobronchial catheter will become more apparent in light of the following detailed description of a preferred embodiment thereof and as illustrated in the accompanying drawings.

DETAILED DESCRIPTION OF THE INVENTION

Figure 1:
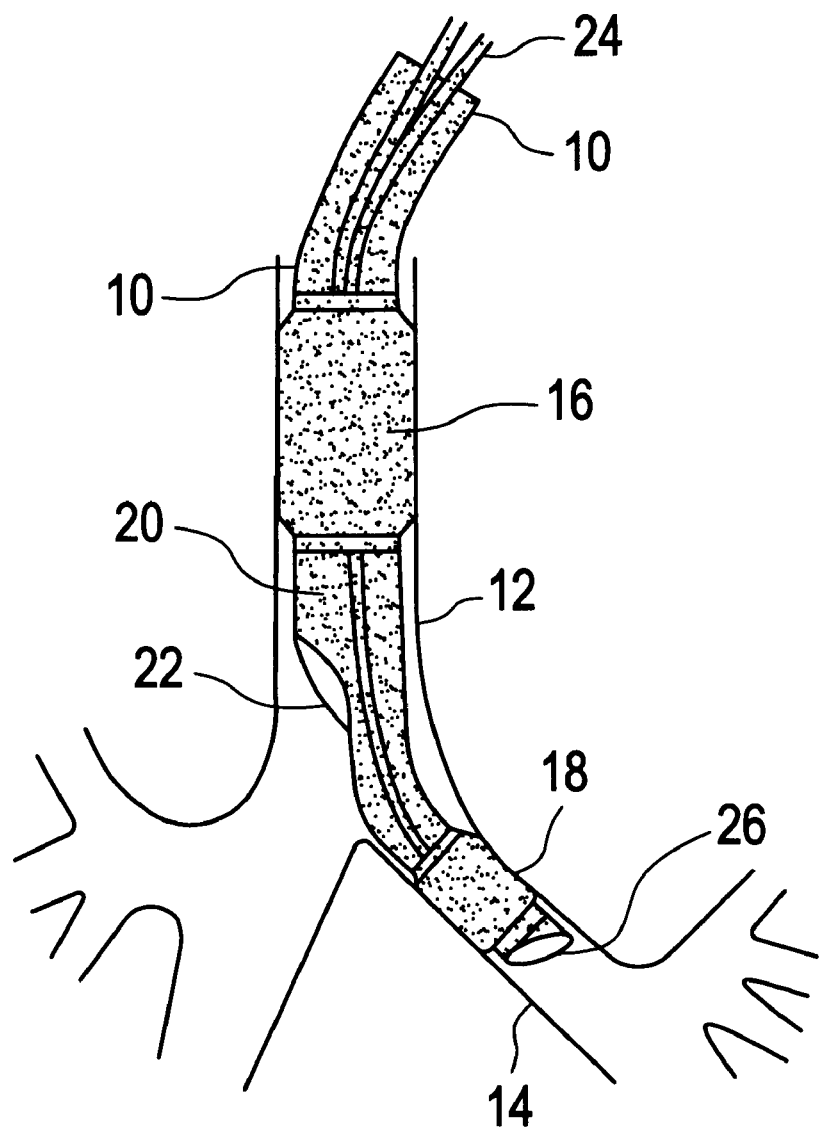
FIG. 1 is a schematic view of a conventional double lumen endotracheal tube shown in its operative position intubated into a patient.

Referring now to FIG. 1, there is shown a schematic view of a double lumen endotracheal tube 10 in its operative position intubated into a patient. As can be seen, the endotracheal tube 10 is positioned within the trachea 12 and extends into the left main bronchus 14 and which is preferred over the alternate position where the right bronchus is entered. The endotracheal tube 10 has a tracheal cuff 16 and a bronchial cuff 18, the former being located in the trachea 12 and the latter in the left main bronchus 14. Both of the cuffs 16 and 18 are, as is conventional, independently and separately inflatable to occlude the particular passageway within which the cuffs are positioned. In addition, there are two individual lumens within the double lumen endotracheal tube 10; that being the tracheal lumen 20 having a distal opening 22 and a bronchial lumen 24 having a distal opening 26. Accordingly, ventilation can be carried out through proximal openings or connections to the anesthesia ventilator such that the inspired gas can be introduced through either the tracheal lumen 24 or the bronchial lumen 26 at the desire of the physician.

The intubation and ultimate positioning of the double lumen endotracheal tube 10 is normally carried out by a direct laryngoscopy and the induction of general anesthesia and a neuromuscular blockade. The proper positioning of the double lumen endotracheal tube 10 is normally confirmed by a series of tests conducted by the separate inflation of the individual cuffs and by providing ventilation to the patient to observe the action of the lungs on an individual basis. When properly positioned, the physician can effectively isolate either of the lungs while allowing the other lung to be normally breathed by the action of the anesthesia ventilator during a surgical operation.

In the use of the double lumen endotracheal tube 10, as can now be appreciated, the left lung can be selectively ventilated by the inflation of the bronchial cuff 18 followed by the providing of ventilation through the bronchial lumen 24 while the further inflation of the tracheal cuff 16 with ventilation provided through the tracheal lumen 20 will ventilate only the right lung and thus, either lung may be individually chosen to be ventilated while the other lung may, at the same time, be isolated in order to carry out a surgical operation on the non-ventilated lung.

As indicated, however, while effective, there are many cases where the placement of the double lumen endotracheal tube 10 is difficult or its later removal raises a risk. For example, where the double lumen endotracheal tube is to be replaced after completion of the surgery in order to return to normal ventilation of the patient, there is some risk, admittedly small, of aspiration. There are instances where the double lumen endotracheal tube is difficult to intubate through the vocal cords because of an unanticipated difficult airway visualization or the presence of a paralyzed vocal cord or if a narrowing of the lower airway anatomical passageway makes the positioning of the double lumen endotracheal tube difficult.

Figure 2:
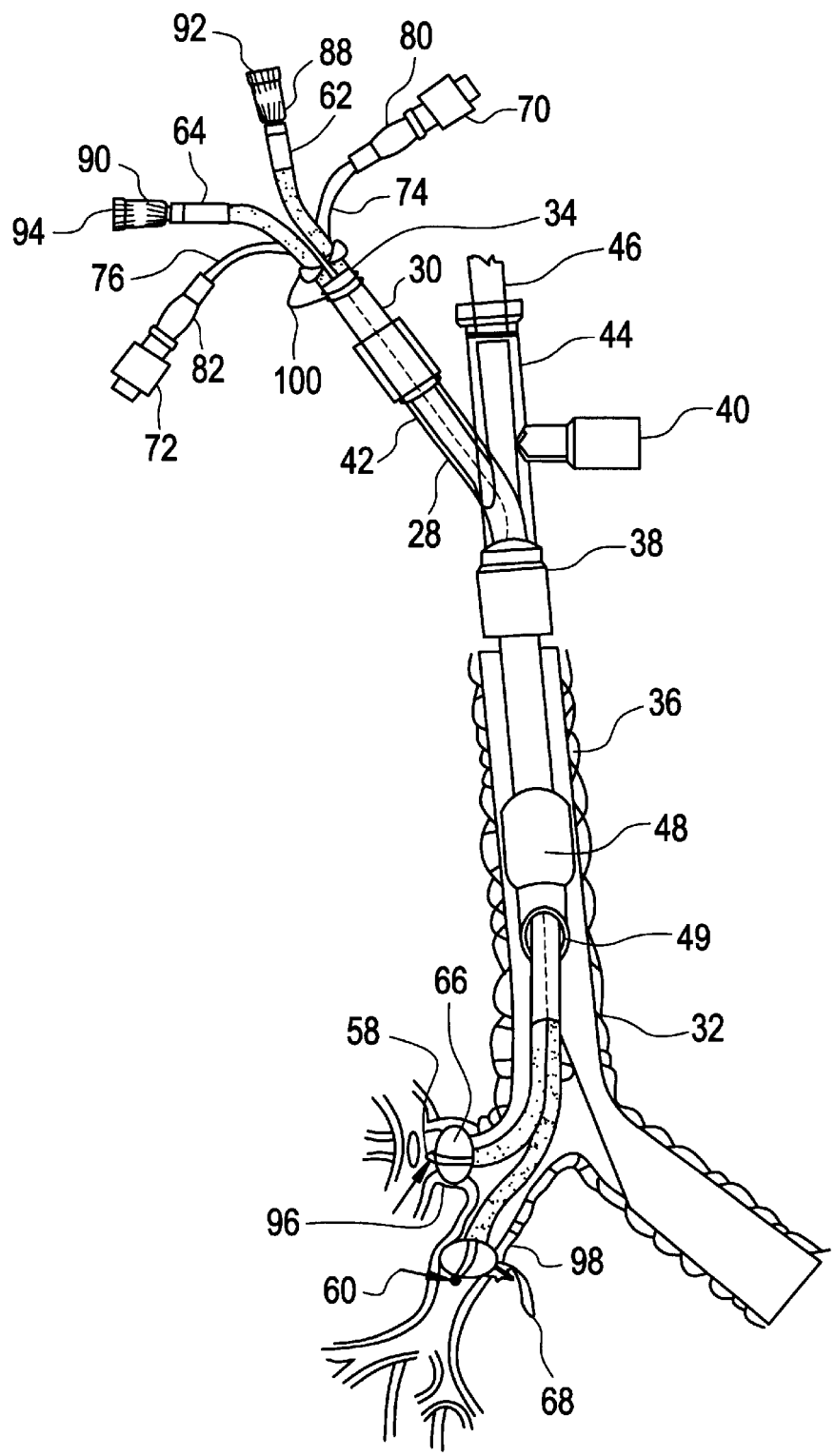
FIG. 2 is a schematic view of a double lumen endobronchial catheter constructed in accordance with the present invention.

Turning now to FIG. 2, there is shown a schematic view of a double endobronchial catheter 28 constructed in accordance with the present invention. In the Fig., the endobronchial catheter 28 includes an outer sheath 30 having distal end 32 and a proximal end 34. The distal end 32 is, of course, located internal of the patient and preferably within the trachea 36 while the proximal end 34 is adapted to remain external of the patient. The outer sheath 30 can be formed or extruded of various plastic materials such as polyvinyl chloride or other suitable materials.

In the embodiment shown, the outer sheath 30 is adapted to be intubated into the patient by sliding the outer sheath 30 through an airway adapter 38 having a port 40 to be connected to a breathing circuit, a side passageway 42 and a central passageway 44 through which a fiberoptic bronchoscope 46 can be positioned in order for the physician to visually perceive the various passageways of the patient in order to properly position the present invention in a manner that will later be explained. As is conventional, the airway adapter 38 also has an inflatable balloon 48 to seal against the internal surface of the trachea 36 to carry out the ventilation of the patient during the surgical procedure.

It should be noted that in the present description as shown in FIG. 2, the outer sheath 30 will be described as being introduced into and through the side passageway 42, however, the introduction of the present invention into a patient can be carried out without the use of an introductory device such as an airway adapter or single lumen endotracheal tube.

In any event, in the shown embodiment, the distal end 32 of the outer sheath 30 preferable extends outwardly of the distal end 49 of the airway adapter 38.

Figure 3:
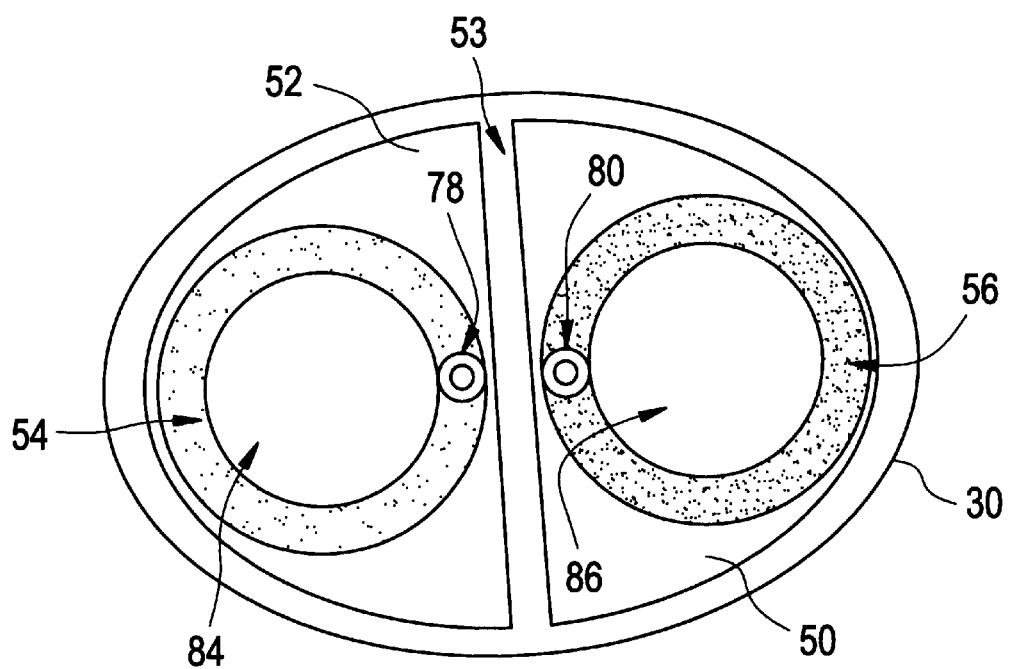
FIG. 3 is cross-sectional view of the catheter of FIG. 2.

The outer sheath 30 has a plurality of individual lumens formed therethrough and, turning briefly to FIG. 3, there is shown a cross sectional view of the double endobronchial catheter 28 and illustrating the generally oval outer sheath 30 basically divided into two lumens 50, 52. The individual lumens may be formed in any conventional manner including being extruded into the outer sheath 30 during the formation of the outer sheath 30 and separated by a common divider 53 molded into the material of the outer sheath 30. The lumens 50, 52 are preferably generally of equal cross sectional areas.

Taking FIG. 3. Now, in conjunction with FIG. 2, there are a pair of blocker catheters 54 and 56 that are slidingly fitted within the individual lumens 50 and 52 of the outer sheath 30. The blocking catheters 54, 56 are also preferable comprised of a plastic material such as polyvinyl chloride or other suitable material and have an outer diameter dimensioned so that the blocker catheters 54, 56 can slide fairly easily within the lumens 50 and 52 and to aid in that sliding relationship, the outer surface of the blocking catheters may be coated with a lubricious material such as silicone.

Both of the blocking catheters 54, 56 are basically similar, each having a distal end 58, 60, a proximal end 62, 64 and each having an inflatable balloon 66, 68 located at or near the distal ends 58, 60. The inflatable balloons are preferably low pressure, soft balloons which are inflated and deflated by means of a conventional system including fittings 70, 72 into which a syringe can be fitted to force air into or take air from the inflatable balloons 66, 68 through tubing 74, 76 that communicates with the inflatable balloons 66, 68 by lumens 78, 80 extending through the blocking catheters 54, 56. The lumens 78, 80 may be extruded into the walls of the catheters themselves. Pilot balloons 80, 82 may also be included to provide an indication to the user that the inflatable balloons 66, 68 are or are not inflated.

As a further feature of the blocking catheters 54, 56, each has an internal orifice 84, 86 that extends thoughout the length of the blocking catheters 54, 56 to an open distal end 58, 60 and include suction ports 88, 90 at the proximal ends 62, 64 so that suction or positive pressure can be applied to the lung of the patient as desired in order to inflate or deflate the lung fully or partially as required during the course of the surgical operation. The internal orifices 84, 86 are therefore accessible at the proximal ends 62, 64 thereof where there may be stylet caps 92, 94 that can close off the internal orifices 84, 86 at those proximal ends 62, 64 by the user.

Stylets, not shown, also are preferably used with the present invention and are located within the internal orifices 84, 86. As will be seen, by controlling the stylets at the proximal ends 62, 64 of the blocking catheters 54, 56, the distal ends 58, 60 of the blocking catheters 54, 56 can be manipulated by the physician such that the distal ends 58, 60 can be positioned to locate the inflatable balloons 66, 68 in the positions as shown in FIG. 2, that is, one inflatable balloon 66 is in the right upper lobe orifice 96 and the other inflatable balloon 68 is in the bronchus intermedius 98. At that position, the inflatable balloons 66, 68 can be inflated such that the right upper lobe orifice 96 and the bronchus intermedius 98 can both be occluded together or individually. In the preferred embodiment, the stylets are removable after the distal ends 58, 60 of the blocker catheters 54, 56 have been positioned at the desired sites.

Once the inflatable balloons 66, 68 are in the proper, desired location within the patient, a securing means, preferably in the form of a double clip 100 can be affixed to the blocking catheters 54, 56 at the point they emerge proximally from the proximal end 34 of the outer sheath 30 and that double clip 100 is used to affix the blocking catheters 54, 56, to the outer sheath 30 to insure that they are securely retained at the desired location within the patient.

With the aforegoing description of the double lumen endobronchial catheter 28 an explanation of the use of the present invention can now be set forth. In carrying out the method steps of the present invention, the outer sheath 30 with the blocker catheters 54, 56 slidingly contained therein, is intubated into the trachea of the patient. The sliding manipulation of the blocking catheters 54, 56 is provided by the clearances within the lumens 50, 52 of the outer sheath 30 along with the lubricious coating applied to the external surface of each of the blocking catheters 54, 56. As indicated, that intubation may be through a single lumen tracheal tube or other airway device or the outer sheath 30 may simply be intubated directly without the use of such airway device.

Once the outer sheath 30 is properly positioned, each of the blocking catheters 54, 56 can be individually manipulated by the physician aided by the use of the stylets that can be located within the lumens 84, 86 to enable such manipulation of the distal ends 58, 60 to locate the inflatable balloons 66, 68 at the desired sites, that is, one inflatable balloon 66 is located in the upper lobe orifice 96 and the other inflatable balloon is located in the bronchus intermedius 98. Upon that positioning, which is guided by the use of a fiber optic bronchoscope, the stylets can be removed and the double clip 100 affixed in position to hold the blocking catheters 54, 56 in the desired position.

Accordingly, by now inflating the inflatable balloons 66, 68 the upper lobe orifice 96 and the bronchus intermedius 98 can both selectively and individually be occluded so that there is an isolation of one of the lungs of the patient and induction and general anesthesia can be carried out on the patient with the use only of the other lung. At the same time the physician also has available the internal orifices 84 and 86 of both blocking catheters 54, 56 in the event the physician desires to apply suction to the lung or even to add air to partially inflate the lung so that the lung is at the proper state of inflation or deflation to best carry out the operation.

While the present invention has been set forth in terms of a specific embodiment or embodiments, it will be understood that the double endobronchial catheter and the method of isolating one lung of a patient may be modified or altered by those skilled in the art to other configurations or methods. Accordingly, the invention is to be broadly construed and limited only by the scope and spirit of the claims appended hereto.

I claim:

1. A double endobronchial catheter, said catheter comprising:
    an outer sheath, said outer sheath having a distal end adapted to be introduced into a patient and a proximal end adapted to remain exterior to a patient, said outer sheath having a plurality of individual lumens,
    a first catheter adapted to slidingly fit within one of said plurality of lumens in said outer sheath, said first catheter having a distal end adapted to be positioned at a predetermined site within a patient and having a proximal end, said first catheter having an inflatable balloon located at said distal end of said first catheter,
    a second catheter adapted to slidingly fit within one of said plurality of lumens in said outer sheath, said first catheter having a distal end adapted to be positioned at a predetermined site within a patient and having a proximal end, said second catheter having an inflatable balloon located at said distal end of said first catheter,
    wherein each of said first and second catheters are separately and independently manipulatable within said outer sheath to enable said distal ends of said first and second catheters to be positioned at the predetermined sites within a patient.

2. A double endobronchial catheter as defined in claim 1 wherein said first and second catheters are coated with silicone.

3. A double endobronchial catheter as defined in claim 1 wherein said plurality of lumens in said outer sheath comprises two lumens.

4. A double endobronchial catheter as defined in claim 3 wherein said two lumens are separated within said outer sheath by a divider that is molded into said outer sheath.

5. A double endobronchial catheter as defined in claim 1 wherein said predetermined sites of the distal ends of said first and second catheters are the upper lobe orifice and the bronchus intermedius of a patient.

6. A double endobronchial catheter as defined in claim 1 wherein said first and second catheters have suction passageways that extend from said proximal ends to said distal ends and include connectors at said proximal ends for making a fluid connection with said suction passageways.

7. A double endobronchial catheter as defined in claim 1 wherein said catheter includes air passages in each of said first and second catheter for inflating said first and second balloons.

8. A double endobronchial catheter as defined in claim 1 wherein said first and second catheters includes a stylet that is located in each of said first and second catheters to aid in the manipulation of said first and second catheters.

9. A double endobronchial catheter as defined in claim 8 wherein said stylet is removable.

10. A method of isolating one lung of a patient preparatory to a surgical operation on that isolated lung, said method comprising the steps of:

providing an outer sheath having a plurality of individual lumens and having a distal end and a proximal end;

introducing the outer sheath into the trachea of a patient to position the distal end thereof distally within the patient;

providing a first catheter slidingly located within one of the plurality of lumens in the outer sheath having a distal end with an inflatable balloon and a proximal end, providing a second catheter slidingly located within one other of the plurality of lumens in the outer sheath having a distal end with an inflatable balloon and a proximal end, independently manipulating each of said first and second catheters to locate said balloons at desired passageways leading to one lung of a patient; and inflating at least one of said balloons to occlude at least one passageway leading to the one lung of a patient.

11. A method of isolating one lung of a patient as defined in claim 10 wherein said method further comprises the step of securing the first and second catheters to the outer sheath when the first and second catheters are located in the desired site within the patient.

12. A method of isolating one lung of a patient as defined in claim 10 wherein said step of independently manipulating each of said first and second catheters comprises locating said first catheter within the upper lobe orifice of a patient and locating said second catheter within the bronchus intermedius of a patient.

13. A method of isolating one lung of a patient as defined in claim 12 wherein said step of inflating at least one of said balloons comprises inflating both of said to block both the upper lobe orifice and the bronchus intermedius leading to the one lung.

14. A method of isolating one lung of a patient as defined in claim 10 wherein said steps of providing a first and a second catheter comprises providing a first and a second catheter each having an orifice extending through said first and second catheters.

15. A method of isolating one lung of a patient as defined in claim 14 wherein suction is applied through one of the first or second catheters to control the inflation of the one lung.

16. A method of isolating one lung of a patient as defined in claim 10 wherein said step of providing an outer sheath comprises providing an outer sheath having two lumens therein.

17. A method of isolating one lung of a patient as defined in claim 10 wherein said step of providing a first and a second catheter comprises providing a first and a second catheter having an outer surface coated with a lubricious material.

* * * * *